(12) United States Patent
Leonard et al.

(10) Patent No.: US 7,250,392 B1
(45) Date of Patent: Jul. 31, 2007

(54) SURFACTANT BLEND FOR CLEANSING WIPES

(75) Inventors: Mark Leonard, Kent (GB); Virginia Lazarowitz, Hatfield, PA (US)

(73) Assignee: Cognis Corporation, Ambler, PA (US)

( * ) Notice: Subject to any disclaimer, the term of this patent is extended or adjusted under 35 U.S.C. 154(b) by 0 days.

(21) Appl. No.: 10/795,714

(22) Filed: Mar. 8, 2004

Related U.S. Application Data

(60) Provisional application No. 60/452,911, filed on Mar. 7, 2003.

(51) Int. Cl.
    *C11D 17/00* (2006.01)
(52) U.S. Cl. .................. 510/439; 134/6; 510/130; 510/470; 424/400
(58) Field of Classification Search ......... 510/439, 510/130, 470; 424/400; 134/6
    See application file for complete search history.

(56) References Cited

U.S. PATENT DOCUMENTS

| | | |
|---|---|---|
| 1,985,424 A | 12/1934 | Piggott |
| 2,965,576 A | 12/1960 | Wilson |
| 5,194,639 A | 3/1993 | Connor et al. |
| 5,266,690 A | 11/1993 | McCurry, Jr. et al. |
| 5,334,764 A | 8/1994 | Scheibel et al. |
| 5,449,763 A | 9/1995 | Wulff et al. |
| 5,454,982 A * | 10/1995 | Murch et al. ............... 510/350 |
| 5,750,733 A * | 5/1998 | Vermeer et al. ............ 549/346 |
| 6,063,335 A * | 5/2000 | Pirolo et al. ................ 422/28 |
| 6,087,320 A * | 7/2000 | Urfer et al. ................. 510/470 |
| 6,165,345 A * | 12/2000 | Updegrove et al. ......... 205/717 |
| 6,310,022 B1 * | 10/2001 | Amiran ....................... 510/185 |
| 6,340,663 B1 * | 1/2002 | Deleo et al. ................ 510/438 |
| 6,391,835 B1 * | 5/2002 | Gott et al. .................. 510/143 |
| 6,407,051 B1 * | 6/2002 | Smith et al. ................ 510/417 |
| 6,440,925 B1 * | 8/2002 | Suazon et al. ............. 510/438 |
| 6,673,761 B2 * | 1/2004 | Mitra et al. ................ 510/384 |
| 2002/0183233 A1 * | 12/2002 | Mitra et al. ................ 510/438 |
| 2003/0069161 A1 * | 4/2003 | Lee et al. ................... 510/438 |
| 2003/0119705 A1 * | 6/2003 | Barnabas et al. .......... 510/438 |
| 2004/0106533 A1 * | 6/2004 | Mitra et al. ................ 510/183 |
| 2004/0136940 A1 * | 7/2004 | Lazarowitz ............. 424/70.13 |

* cited by examiner

*Primary Examiner*—Sharidan Carrillo
(74) *Attorney, Agent, or Firm*—John F. Daniels; Daniel S. Ortiz

(57) ABSTRACT

A cleansing product containing: (a) a water insoluble substrate; and (b) a surfactant composition impregnated onto the substrate, the composition containing: (i) at least one lathering surfactant; and (ii) at least about 40% by weight, based on the weight of the composition, of water.

9 Claims, No Drawings

SURFACTANT BLEND FOR CLEANSING WIPES

CROSS-REFERENCE TO RELATED APPLICATIONS

This application claims the benefit of copending provisional application Ser. No. 60/452,911 filed Mar. 7, 2003.

STATEMENT REGARDING FEDERALLY SPONSORED RESEARCH OR DEVELOPMENT

Not applicable.

BACKGROUND OF THE INVENTION

Personal cleansing and conditioning products have traditionally been marketed in a variety of forms such as bar soaps, creams, lotions and gels. These formulations have attempted to satisfy a number of criteria to be acceptable to consumers. These criteria include cleansing effectiveness, skin feel, skin mildness and lather volume. Ideal personal cleansers should gently cleanse the skin or hair, cause little or no irritation, and not leave the skin or hair overly dry after frequent use.

SUMMARY OF THE INVENTION

The present invention is directed to an aqueous surfactant composition for use on substrates, the surfactant blend containing:

(a) from about 10 to about 30% by weight of a sugar surfactant selected from the group consisting of an alkyl polyglycoside corresponding to formula I:

$$R_1O(R_2O)_b(Z)_a \qquad \qquad I$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6, a polyhydroxy fatty acid amide corresponding to formula II:

wherein $R_3$ is H, $C_1$-$C_4$ hydrocarbyl, 2-hydroxy ethyl, 2-hydroxy propyl, or a mixture thereof; and $R_4$ is a $C_5$-$C_{31}$ hydrocarbyl moiety; and Y is a polyhydroxyhydrocarbyl moiety having a linear hydrocarbyl chain with at least 3 hydroxyls directly connected to the chain, and mixtures thereof;

(b) up to about 20% by weight of an amphoteric surfactant;

(c) up to about 20% by weight of an anionic surfactant;

(d) up to about 40% by weight of a water-soluble oil component; and (e) from about 30 to 50% by weight water, all weights being based on the weight of the composition.

The present invention is also directed to a substrate containing an effective amount of the above-disclosed aqueous surfactant composition.

BRIEF DESCRIPTION OF THE SEVERAL VIEWS OF THE DRAWING

Not applicable.

DETAILED DESCRIPTION OF THE INVENTION

Other than in the operating examples, or where otherwise indicated, all numbers expressing quantities of ingredients or reaction conditions are to be understood as being modified in all instances by the term "about".

The present invention is directed to a novel surfactant composition capable of safely and mildly cleansing human skin. One essential ingredient of the surfactant composition of the present invention is a sugar surfactant. Particularly preferred sugar surfactants include alkyl polyglycosides and glucamides. The use of these nonionic surfactants is highly desirable due to the fact that they are derived from renewable resources, are very mild and provide acceptable levels of foam.

The alkyl polyglycosides suitable for use in the present invention are those which correspond to formula I:

$$R_1O(R_2O)_b(Z)_a \qquad \qquad I$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6. Such alkyl polyglycosides are commercially available, for example, as APG®, GLUCOPON®, PLANTAREN®, PLANTACARE® or AGRIMUL® surfactants from Cognis Corporation, Ambler, Pa., 19002. Examples of such surfactants include but are not limited to:

1. GLUCOPON® 220 Surfactant—an alkyl polyglycoside in which the alkyl group contains 8 to 10 carbon atoms and having an average degree of polymerization of 1.5.
2. GLUCOPON® 225 Surfactant—an alkyl polyglycoside in which the alkyl group contains 8 to 10 carbon atoms and having an average degree of polymerization of 1.7.
3. GLUCOPON® 600 Surfactant—an alkyl polyglycoside in which the alkyl group contains 12 to 16 carbon atoms and having an average degree of polymerization of 1.4.
4. GLUCOPON® 625 Surfactant—an alkyl polyglycoside in which the alkyl group contains 12 to 16 carbon atoms and having an average degree of polymerization of 1.6.
5. APG® 325 Surfactant—an alkyl polyglycoside in which the alkyl group contains 9 to 11 carbon atoms and having an average degree of polymerization of 1.6.
6. PLANTAREN® 2000 Surfactant—an alkyl polyglycoside in which the alkyl group contains 8 to 16 carbon atoms and having an average degree of polymerization of 1.5.
7. PLANTAREN® 1200 Surfactant—an alkyl polyglycoside in which the alkyl group contains 12 to 16 carbon atoms and having an average degree of polymerization of 1.4.
8. AGRIMUL® PG 2067 Surfactant—an alkyl polyglycoside in which the alkyl group contains 8 to 10 carbon atoms and having an average degree of polymerization of 1.7.

Other examples include alkyl polyglycoside surfactant compositions which are comprised of mixtures of compounds of formula I as described in U.S. Pat. Nos. 5,266,690 and 5,449,763, the entire contents of both of which are incorporated herein by reference.

A particularly preferred alkyl polyglycoside for use in the present invention is one wherein $R_1$ is a monovalent organic radical having from about 8 to about 16 carbon atoms, b is zero, and a is a number having a value of from about 1.4 to about 1.6. This specific type of alkyl polyglycoside is commercially available from Cognis Corporation, Ambler, Pa., under the tradenames PLANTAREN® 2000 N UP or PLANTACARE® 2000 UP.

Suitable glucamides which can be used in the composition of the present invention are those corresponding to general formula (II):

wherein: $R_3$ is H, $C_1$-$C_4$ hydrocarbyl, 2-hydroxy ethyl, 2-hydroxy propyl, or a mixture thereof, preferably $C_1$-$C_4$ alkyl, more preferably $C_1$ or $C_2$ alkyl, most preferably $C_1$ alkyl (i.e., methyl); and $R_4$ is a $C_5$-$C_{31}$ hydrocarbyl moiety, preferably straight chain $C_7$-$C_{19}$ alkyl or alkenyl, more preferably straight chain $C_9$-$C_{17}$ alkyl or alkenyl, most preferably straight chain $C_{11}$-$C_{19}$ alkyl or alkenyl, or mixture thereof; and Y is a polyhydroxyhydrocarbyl moiety having a linear hydrocarbyl chain with at least 3 hydroxyls directly connected to the chain, or an alkoxylated derivative (preferably ethoxylated or propoxylated) thereof. Y preferably will be derived from a reducing sugar in a reductive amination reaction; more preferably Y is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Y. It should be understood that it is by no means intended to exclude other suitable raw materials. Y preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic mono-or polysaccharide, and alkoxylated derivatives thereof. Most preferred are glycityls wherein n is 4, particularly —$CH_2$—$(CHOH)_4$—$CH_2OH$. Herefore, when, for example, $R_3$ is methyl, $R_4$ dodecyl; and Y is —$CH_2$—$(CHOH)_4$—$CH_2OH$, the compound in question is referred to as dodecyl N-methylglucamide.

Methods for making glucamides (polyhydroxy fatty acid amides) are known in the art. In general, polyhydroxy fatty acid amides can be made by reductively aminating a reducing sugar reacting with an alkyl amine to form a corresponding N-alkyl polyhydroxyamine and then reacting the N-alkyl polyhydroxyamine with a fatty aliphatic ester or triglyceride to form the N-alkyl, polyhydroxy fatty acid amide. Processes for making polyhydroxy fatty acid amides are disclosed in U.S. Pat. Nos. 1,985,424; 2,965,576; 5,194,639; and 5,334,764 the entire contents of each of which is incorporated herein by reference.

It is highly desirable to also employ at least one co-surfactant in the surfactant mixture of the present invention. The co-surfactant should also be mild to human skin and further enhance lather generation by the composition. Preferred co-surfactants for use in the present invention include anionic surfactants, amphoteric surfactants, and mixtures thereof.

Suitable anionic co-surfactants which may be employed in the composition include, but are not limited to, alkyl benzene sulfonates, alkyl sulfates, paraffin sulfonates, olefin sulfonates, alkyl ether sulfates, alkyl glyceryl ether sulfonates, fatty acid ester sulfonates, secondary alcohol sulfates, alkyl glucose carboxylates, fatty acyl isethionates, dialkyl sulfosuccinates, alkanoyl sarcosinates, alkyl lactylates, taurates, glutamates and mixtures thereof.

A particularly preferred anionic co-surfactant for use in the present invention is disodium cocoylglutamate, commercially available from Cognis Corporation, Ambler, Pa., under the tradename PLANTAPON®ACG 35.

Another preferred anionic co-surfactant for use in the present invention is sodium lauryl glucose carboxylate, commercially available from Cognis Corporation, Ambler, Pa., under the tradename PLANTAPON®LGC Sorb.

Suitable amphoteric surfactants which may be employed in the composition include, but are not limited to, aliphatic secondary and tertiary amines, preferably wherein the nitrogen is in a cationic state, in which the aliphatic radicals can be straight or branched chain and wherein one of the radicals contains an ionizable water solubilizing group such as carboxy, sulphonate, sulphate, phosphate or phosphonate. Specific examples thereof include cocamidopropyl betaine, cocamphoacetate, cocamphodiacetate, cocamphopropionate, cocamphodipropionate, cocamidopropyl hydroxysultaine, cetyl dimethyl betaine, cocamidopropyl PG-dimonium chloride phosphate, coco dimethyl carboxylmethyl betaine, cetyl dimethyl betaine, and mixtures thereof.

A particularly preferred amphoteric surfactant for use in the present invention is cocamidopropyl betaine, commercially available from Cognis Corporation, Ambler, Pa., under the tradenames, DEHYTON®K or VELVETEX® BA-35.

It may also be desirable to include a water-soluble oil component in the composition of the present invention in order to impart a skin conditioning/humectant property to the composition. Examples of the suitable water-soluble oil components include, but are not limited to, as polyhydric alcohols are particularly preferred. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof.

A particularly preferred water-soluble oil component for use in the present invention is a mixture of glycerin and PEG-7 glyceryl cocoate, commercially available from Cognis Corporation, Ambler, Pa. under the tradename CETIOL®HE.

Auxiliary components may also be employed in the composition of the present invention in order to further enhance its performance. Examples thereof include, but are not limited to, preservatives such as phenoxyethanol, sodium EDTA, polyaminopropyl biguanide, hexamidine diisethionate, and the like, pH buffers such as citric acid, and compounds which impart mildness when applied onto human skin such as parabens (methylparaben, butylparaben, ethylparaben, propylparaben), and/or mixtures thereof.

According to one embodiment of the present invention, there is provided an aqueous surfactant composition containing: (a) from about 10 to about 30% by weight, preferably from about 10 to about 25% by weight, and most preferably from about 15 to 20% by weight of a sugar surfactant, preferably an alkyl polyglycoside; (b) up to about 20% by weight, preferably from about 5 to about 15% by weight, and most preferably from about 5 to 10% by weight, of an amphoteric surfactant, preferably a cocamidopropyl betaine; (c) up to about 20% by weight, preferably from about 5 to about 15% by weight, and most preferably from about 5 to 10% by weight, of an anionic surfactant, preferably a glutamate; (d) up to about 40% by weight, preferably from about 5 to about 35% by weight, and most preferably from about 15 to about 30% by weight of a water-soluble oil component, preferably a mixture of glycerin and PEG-7 glyceryl cocoate; and (e) from about 30 to about 50% by weight, preferably from about 35 to about 50% by weight, and most preferably from about 40 to 45% by weight of water, all weights being based on the total weight of the composition.

It is important to note that the viscosity of the aqueous surfactant composition should be no greater than 1,000 cps in order to enable the composition to be satisfactorily applied onto a water-insoluble substrate. In the event that the viscosity is too high, the composition will not lend itself to being applied onto the substrate using conventional wipe forming machinery.

The surfactant composition of the present is intended to be applied onto a water insoluble substrate. By "water insoluble" is meant the substrate does not dissolve or readily break apart upon immersion in water. Examples of suitable water insoluble substrates include, but are not limited to, nonwoven substrates, woven substrates, hydro-entangled substrates, air entangled substrates and the like.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof.

Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan.RTM., Creslan.RTM., and the acrylonitrile-based fiber, Orion.RTM.; cellulose ester fibers such as cellulose acetate, Arnel.RTM., and Acele.RTM.; polyamides such as Nylons (e.g., Nylon 6, Nylon 66, and Nylon 610); polyesters such as Fortrel.RTM., Kodel.RTM., and Dacron.RTM.; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers.

Substrates made from natural materials useful in the present invention can be obtained from a wide variety of commercial sources. Non-limiting examples of suitable commercially available paper layers useful herein include Airtex.RTM., an embossed airlaid cellulosic layer having a base weight of about 71 gsy, available from James River Corporation, Green Bay, Wis.; and Walkisoft.RTM., an embossed airlaid cellulosic having a base weight of about 75 gsy, available from Walkisoft U.S.A., Mount Holly, N.C.

Non-woven substrates made from synthetic material useful in the present invention can also be obtained form a wide variety of commercial sources. Non-limiting examples of suitable non-woven layer materials useful herein include HFE-40-047, an apertured hydroentangled material containing about 50% rayon and 50% polyester, and having a basis weight of about 43 grams per square yard (gsy), available from Vertec, Inc., Walpole, Mass.; HEF 140-102, an apertured hydro-entangled material containing about 50% rayon and 50% polyester, and having a basis weight of about 56 gsy, available from Veratec, Inc., Walpole, Mass.; Novenet.RTM. 149-191, a thermo-bonded grid patterned material containing about 69% rayon, about 25% polypropylene, and about 6% cotton, and having a basis weight of about 100 gsy, available from Veratec, Inc., Walpole, Mass.; HEF Nubtex.RTM. 149-801, a nubbed, apertured hydro-entangled material, containing about 100% polyester, and having a basis weight of about 70 gsy, available from Veratec, Inc. Walpole, Mass.; Keybak.RTM. 951V, a dry formed apertured material, containing about 75% rayon, about 25% acrylic fibers, and having a basis weight of about 43 gsy, available from Chicopee Corporation, New Brunswick, N.J.; Keybak.RTM. 1368, an apertured material, containing about 75% rayon, about 5% polyester, and having a basis weight of about 39 gsy, available from Chicopee Corporation, New Brunswick, N.J.; Duralace.RTM. 1236, an apertured, hydro-entangled material, containing about 100% rayon, and having a basis weight from about 40 gsy to about 115 gsy, available from Chicopee Corporation, New Brunswick, N.J.; Duralace.RTM. 5904, an apertured, hydro-entangled material, containing about 100% polyester, and having a basis weight from about 40 gsy to about 115 gsy, available from Chicopee Corporation, New Brunswick, N.J.; Sontaro.RTM. 8868, a hydro-entangled material, containing about 50% cellulose and about 50% polyester, and having a basis weight of about 60 gsy, available from Dupont Chemical Corp.

Most preferred as a substrate for purposes of this invention are non-woven substrates, especially blends of rayon/polyester and ratios of 10:90 to 90:10, preferably ratios of 20:80 to 80:20, optimally 40:60 to 60:40 by weight. A most useful substrate is a 70:30 rayon/polyester non-woven wipe article.

Anywhere from 1 to 100, preferably from 5 to 50 single wipes may be stored within a dispensing pouch or container, preferably a moisture impermeable pouch or container. During storage and between dispensing, the pouch or container is preferably resealable. Single wipe containing pouches may also be employed.

The water insoluble substrates of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different colors, thereby helping the user to further distinguish the surfaces. Although the present invention may be suitable for substrates with two or more layers having different texture and abrasiveness, the best effectiveness of the damp system can be found with single or multiple layered substrates of identical construction.

The disposable, single use personal care cleansing products of the present invention are manufactured by separately or simultaneously adding onto or impregnating into a water insoluble substrate the surfactant composition of the present invention, wherein the resulting product is substantially dry.

The surfactant composition of the present invention can be added onto or impregnated into the water insoluble substrate by any means known to those skilled in the art. For example, addition can be through spraying, laser printing, splashing, dipping, soaking, or coating.

The present invention will be better understood from the examples which follow, all of which are intended for illustrative purposes only, and are not meant to unduly limit the scope of the invention in any way.

EXAMPLES

A formula typical of the present invention for impregnation onto a water insoluble substrate was formulated with the following components.

| INGREDIENT | WEIGHT % (as actives) |
|---|---|
| PLANTACARE ® 2000 UP | 18.0 |
| DEHYTON ® K | 6.0 |
| CETIOL ® HE | 15.0 |
| PLANTAPON ® ACG 35 | 5.0 |
| GLYCERIN | 9.5 |
| preservative | 1.5 |
| citric acid | 1.0 |
| water | 44.0 |

What is claimed is:

1. A cleansing product comprising:
   (a) a water-insoluble substrate; and
   (b) a surfactant composition impregnated onto the substrate, the surfactant composition containing:
      (i) from about 10% to about 30% by weight of at least one sugar surfactant selected from the group consisting of alkyl polyglycosides and, glucamides;
      (ii) a co-surfactant comprising,
         (a) about 5% to about 20% by weight of an amphoteric surfactant, and
         (b) up to about 20% by weight of an anionic surfactant;
      (iii) about 5% to about 40% by weight of a water soluble oil component; and
      (iv) at least about 30% by weight of water, all weights based on the total weight of the surfactant composition.

2. The product of claim 1 wherein the sugar surfactant comprises an alkyl polyglycoside corresponding to formula I:

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6.

3. The product of claim 1 wherein the amphoteric surfactant is present in the composition in an amount of from about 5 to 15% by weight, based on the weight of the composition.

4. The product of claim 1 wherein the co-surfactant comprises an anionic surfactant.

5. The product of claim 1 wherein the composition has a viscosity of, at most, about 1,000 cps.

6. The product of claim 1 wherein the water-insoluble substrate is a disposable sheet made from a non-woven material.

7. The product of claim 2 wherein in formula I, $R_1$ is a monovalent organic radical having from about 8 to 16 carbon atoms, b is zero, and a is a number having a value of from about 1.4 to 1.6.

8. The product of claim 4 wherein the anionic surfactant is present in the composition in an amount of from about 5 to 15% by weight, based on the weight of the composition.

9. A cleansing product comprising:
   (a) a water-insoluble substrate;
   (b) a surfactant composition impregnated onto the substrate, the surfactant composition containing:
      (i) from about 15 to about 20% by weight of an alkyl polyglycoside corresponding to formula I:

wherein $R_1$ is a monovalent organic radical having from about 8 to about 16 carbon atoms; $R_2$ is divalent alkylene radical having from 2 to 4 carbon atoms; Z is a saccharide residue having 5 or 6 carbon atoms; b is 0; a is a number having a value from about 1.4 to about 1.6;
      (ii)
         (a) from about 5 to about 10% by weight of an amphoteric surfactant;
         (b) from about 5 to about 10% by weight of an anionic surfactant;
      (iii) from about 15 to about 30% by weight of a water soluble oil component; and
      (iv) from about 30 to about 50% by weight water, all weights being based on the total weight of the surfactant composition.

* * * * *